United States Patent [19]
Dunmore et al.

[11] Patent Number: 5,763,200
[45] Date of Patent: Jun. 9, 1998

[54] INHIBITION OF AMYLIN RELEASE

[75] Inventors: Simon Jon Dunmore; Michelle Davenport, both of Buckingham; Michael Anthony Cawthorne, Horsham, all of United Kingdom

[73] Assignee: Biomeasure, Incorporated, Milford, Mass.

[21] Appl. No.: 440,061

[22] Filed: May 12, 1995

[51] Int. Cl.$^6$ .................... G01N 33/58; G01N 33/554; C07K 14/655

[52] U.S. Cl. .................................. 435/7.21; 435/361

[58] Field of Search ................ 435/7.1, 7.2, 7.21, 435/240.2, 69.1, 7.23, 361

[56] References Cited

FOREIGN PATENT DOCUMENTS

WO 93/13130  7/1993  WIPO.

OTHER PUBLICATIONS

Davenport et al., "Somatostatin Type 5 Receptors Mediate the Inhibitory Action of Somatostatin on Insulin Secretion in Zucker Fatty Rat Perfused Pancreas", Diabetologia (Supp. 1) 38:A106, XP000602793, 1995.

Moldovan et al., "Somatostatin Inhibits B–Cell Secretion via a Subtype–2 Somatostatin Receptor in the Isolated Perfused Human Pancreas", J. of Surgical Research 59:85–90, XP000602464, 1995.

Hoyer et al., "Molecular Pharmacology of Somatostatin Receptors", Naunyn–Schmiedeberg's Arch Pharmacology 350:441–453, 1994.

Inoue et al., "Effects of Exogenous Somatostatin and Insulin on Islet Amyloid Polypeptide (Amylin) Release from Perfused Rat Pancreas", Horm. Metab. Res. 24:251–253, 1992.

Moore et al., "Co–Secretion of Amylin and Insulin from Cultured Islet β–Cells: Modulation By Nutrient Secretagogues, Islet Hormones & Hypoglycemic Agents", Biochemical & Biophysical Res. Commun. 179:1–9, 1991.

Rossowski et al., "Specific Inhibition of Rat Pancreatic Insulin or Glucagon Release by Receptor–Selective Somatostatin Analogs", Biochemical & Biophysical Res. Commun. 205:341–246, 1994.

Raynor et al., "Cloned Somatostatin Receptors: Identification of Subtype–Selective Peptides and Demonstration of High Affinity Binding of Linear Peptides", Molecular Pharmacology 43:838–844, 1993.

Yamada et al. Biochem. Biophy. Res. Commun. 195 (1993) 844–852.

Guidobono et al. Peptides 15 (1994):699–702.

Peiro et al. Life Sciences 49 (1991):761–765.

Dunmore et al. J. Endocrinology 137 (1993):375–381.

Primary Examiner—Paula K. Hutzell
Assistant Examiner—Robert C. Hayes
Attorney, Agent, or Firm—Fish & Richardson; William McGowan; John D. Conway

[57] ABSTRACT

A method of determining the ability of a compound to both bind to somatostatin type-5 receptor ("SSTR-5") and inhibit amylin release. The method includes obtaining a preparation, either a cell preparation or a membrane preparation, which contains SSTR-5; incubating the preparation, the compound, and a SSTR-5 ligand, at least one of the ligand and the compound being detectably labeled; determining the ability of the compound to compete against the ligand for binding to SSTR-5; if and only if the compound is determined to be able to bind to SSTR-5, obtaining pancreatic cells; incubating the compound, the pancreatic cells, and an amylin release stimulator under conditions in which the amylin release stimulator would induce release of amylin from the pancreatic cells; and determining the ability of the compound to inhibit amylin release. Also disclosed is a method of treating hyperamylinemia with a ligand selective for SSTR-5.

5 Claims, 3 Drawing Sheets

INHIBITION OF AMYLIN RELEASE

BACKGROUND OF THE INVENTION

Amylin, a 37-amino acid polypeptide structurally related to calcitonin gene-related protein [Cooper, Endocrine Review, 15:163 (1994)], is primarily synthesized, packaged, and secreted from the β-cells of pancreatic islets. Apart from the islet of Langerhans, amylin-like immunoreactivity activity has also been detected in lung, gastrointestinal tract, and the nervous system. See Miyazato, M., et. al., Bioch. Bioph. Res. Comm., 181:293 (1991); Chance, et al., Brain Res., 539:352 (1991); Mulder, et al., Gastroenterology, 107:712 (1994).

The presence of an abnormally high concentration of amylin in the blood, i.e., hyperamylinemia, has been found in patients with pancreatic cancer [Permert, et al., N. Engl. J. Med, 330:313 (1994)], obese patients [Huang, et al., Hypertension, 19 (Supp. I):101 (1992)], and in prediabetic patients [Erickson, J., Diabetologia, 35:291 (1992)]. The hyperamylinemic state has been associated with both diabetes as well as amyloid formations. DeKoning, et al., Proc. Natl. Acad. Sci. USA, 91:8467 (1994). Amyloid formation causes destruction of β-islet cells and eventually pancreatic dysfunction. Johnson, et al., Lab. Invest. 66:522 (1992); Lorenzo, et al., Nature, 368:756 (1994).

Native somatostatin is comprised of both a 14-amino acid isoform (somatostatin-14) and a 18-amino acid isoform (somatostatin-28). Reichlin, New Eng. J. Medicine, 309(24): 1495 (1983). Five distinct somatostatin receptors have been identified and characterized. Hoyer, et al., Naunyn-Schmiedeberg's Arch. Pharmacol., 350:441 (1994). Somatostatin produces a variety of effects, including modulation of hormone release, e.g., growth hormone, glucagon, insulin, amylin, and neurotransmitter release. Some of these effects have been associated with its binding to a specific somatostatin receptor. For example, the inhibition of growth hormone has been attributed to somatostatin type-2 receptor ("SSTR-2"). Raynor, et al., Molecular Pharmacol. 43:838 (1993); Lloyd, et al. Am. J. Physiol. 268:G102 (1995). Because of the short half-life of the native somatostatin, various somatostatin analogs have been developed, e.g., for the treatment of acromegaly. Raynor, et al., Molecular Pharmacol. 43:838 (1993).

SUMMARY OF THE INVENTION

The present invention is based on the discovery that ligands selective for somatostatin type-5 receptor ("SSTR-5") are effective in inhibiting release of amylin from pancreas cells.

An aspect of this invention relates to a method of determining the ability of a compound to both bind to somatostatin type-5 receptor and inhibit amylin release from amylin-secreting pancreas cells. The method includes the steps of (i) obtaining a preparation, either a cell preparation or a membrane preparation, which contains SSTR-5; (ii) incubating the preparation, the compound, and a SSTR-5 ligand, at least one of the ligand and the compound being detectably labeled; (iii) determining the ability of the compound to compete against the ligand for binding to SSTR-5; (iv) if and only if the compound is determined to be able to bind to SSTR-5, obtaining amylin-secreting pancreatic cells (e.g., cells in an intact pancreas from a rodent such as a rat or a mouse, pancreatic islet cells such as β cells, or amylinoma cells); (v) incubating the compound, the pancreatic cells, and an amylin release stimulator (e.g., glucose or D-glyceraldehyde) under conditions in which the amylin release stimulator would induce release of amylin from the pancreatic cells; and (vi) determining the ability of the compound to inhibit amylin release.

By "SSTR-5 ligand" is meant a compound which binds to SSTR-5, e.g., somatostatin-14, somatostatin-28, an analog of somatostatin-14 or somatostatin-28 (such as [Tyr$^{11}$]-somatostatin-14), or an antibody raised against of SSTR-5. Either the ligand or the test compound can be labeled with a radioactive isotope, or a nonradioactive (e.g., fluorescent, chemiluminescent, or biotinylated) molecule. Preferably, [$^{125}$I-Tyr$^{11}$]-somatostatin-14 is used as a labeled SSTR-5 ligand to practice the above-described method. Other examples of labeled ligands include $^{125}$I-LTT-somatostatin-28 [Patel, et al., Endocrinol., 135(6):2814 (1994)] and $^{125}$I-CGP 23996 [Raynor, et al., Mol. Pharm. 44:385–392 (1993)].

Examples of the pancreatic cells which are used to practice the above method include both rodent and human islet cells (e.g., β and δ cells) and pancreatic tumor cells (e.g., amylinoma cells). The pancreatic cells can be incubated either in vitro or in vivo. Examples of an in vitro system include an isolated rat pancreas, the rat β-cell line RINm5f, and the hamster β-cell line H1T-T15. As an example of an in vivo system, Sprague-Dawley or Zucker fatty rats can be used as animal models to test the amylin inhibition activity of test somatostatin analogs. An amylin release stimulator, e.g. 16.7 mm of glucose, can be injected into the animal. The test somatostatin analog is then injected into the animals at various concentrations. Blood samples can be taken from the animal, and the amount of amylin present before and after the injection of the test somatostatin analog can be determined by radioimmunoassay.

By "amylin release stimulator" is meant a compound which stimulates the release of amylin stored in pancreatic cells. Examples of amylin release stimulators include glucose, D-glyceraldehyde, or L-arginine.

The method described above can be used to screen for new compounds capable of inhibiting amylin release from the pancreas in a patient. To promote efficiency, when the method is used in a screening project, two or more test compounds can be linked together as a single sample, and, if necessary, subsequently divided and retested.

Another aspect of this invention relates to a method of treating (i.e., either preventing or ameliorating) hyperamylinemia by inhibiting release of amylin from the pancreas in a subject (i.e., a mammal, such as a human being) who suffers from, or is predisposed to suffer from, hyperamylinemia. The method includes administering (e.g., parenterally, intravenously, subcutaneously, transdermally, intramucously, or via implantation of a sustained release formulation), to the subject an amount of a SSTR-5 agonist, the amount being effective in treating hyperamylinemia, i.e., in lowering amylin levels in the bloodstream by inhibiting the release of amylin from pancreas cells.

What is meant by "SSTR-5 agonist" is a compound which (i) is more selective for SSTR-5 than for SSTR-2, i.e., its $K_i$ for SSTR-5 is lower than that for SSTR-2 (as determined by one of the receptor binding assays described in the working examples below); and (ii) inhibits the release of amylin from pancreas cells induced by an amylin release stimulator (as determined by one of the functional assays described in the working examples below). Both examples of SSTR-5 agonists and the procedures of selecting them appear in the "Description of the Invention" section below.

The above-described therapeutic method can be used to treat a subject suffering from pancreatic cancer, prediabetic symptoms, or non-insulin dependent diabetics.

An effective amount depends upon the conditions being treated, the route of administration chosen, and the specific activity of the compound used, and ultimately will be decided by the attending physician or veterinarian. While it is possible for a SSTR-5 agonist to be administered as the pure or substantially pure compound, it is preferable to present it as a pharmaceutical formulation or preparation. The formulations to be used in the present invention, for both humans and animals, comprise any of the SSTR-5 agonists to be described below, together with one or more pharmaceutically acceptable carriers and optionally other therapeutic ingredients. The carrier must be "acceptable" in the sense of being compatible with the active ingredient(s) of the formulation (and preferably, capable of stabilizing peptides) and not deleterious to the subject to be treated.

The formulations may conveniently be presented in unit dosage form and may be prepared by any of the methods well known in the art of pharmacy. All methods include the step of bringing the active ingredient(s) into association with the carrier which constitutes one or more accessory ingredients.

In general, the formulations for tablets or powders are prepared by uniformly and intimately blending the active ingredient with finely divided solid carriers, and then, if necessary as in the case of tablets, forming the product into the desired shape and size.

Formulations suitable for intravenous or subcutaneous administration, on the other hand, conveniently comprise sterile aqueous solutions of the active ingredient(s). Preferably, the solutions are isotonic with the blood of the subject to be treated. Such formulations may be conveniently prepared by dissolving solid active ingredient(s) in water to produce an aqueous solution, and rendering the solution sterile. The formulation may be presented in unit or multi-dose containers, for example, sealed ampoules or vials. Delivery of drug by parenteral implantation of a sustained release formulation is well-known in the art. See, e.g., U.S. Pat. No. 3,773,919, U.S. Pat. No. 4,767,628; and PCT Application No. WO 94/00148.

Also within the scope of this invention are a SSTR-5 agonist for use in treating a disease or a disorder relating to hyperamylinemia, and the use of a SSTR-5 agonist for the manufacture of a medicament for the treatment of such disease or disorder.

Use of a ligand more selective for SSTR-5 than for SSTR-2 to treat hyperamylinemia minimizes undesirable side effects.

Other features and advantages of the invention will be apparent from the following drawings and detailed description of several embodiments and from the appending claims.

BRIEF DESCRIPTION OF THE DRAWINGS

The drawings are first briefly described.

DESCRIPTION OF THE INVENTION

Figure 1:
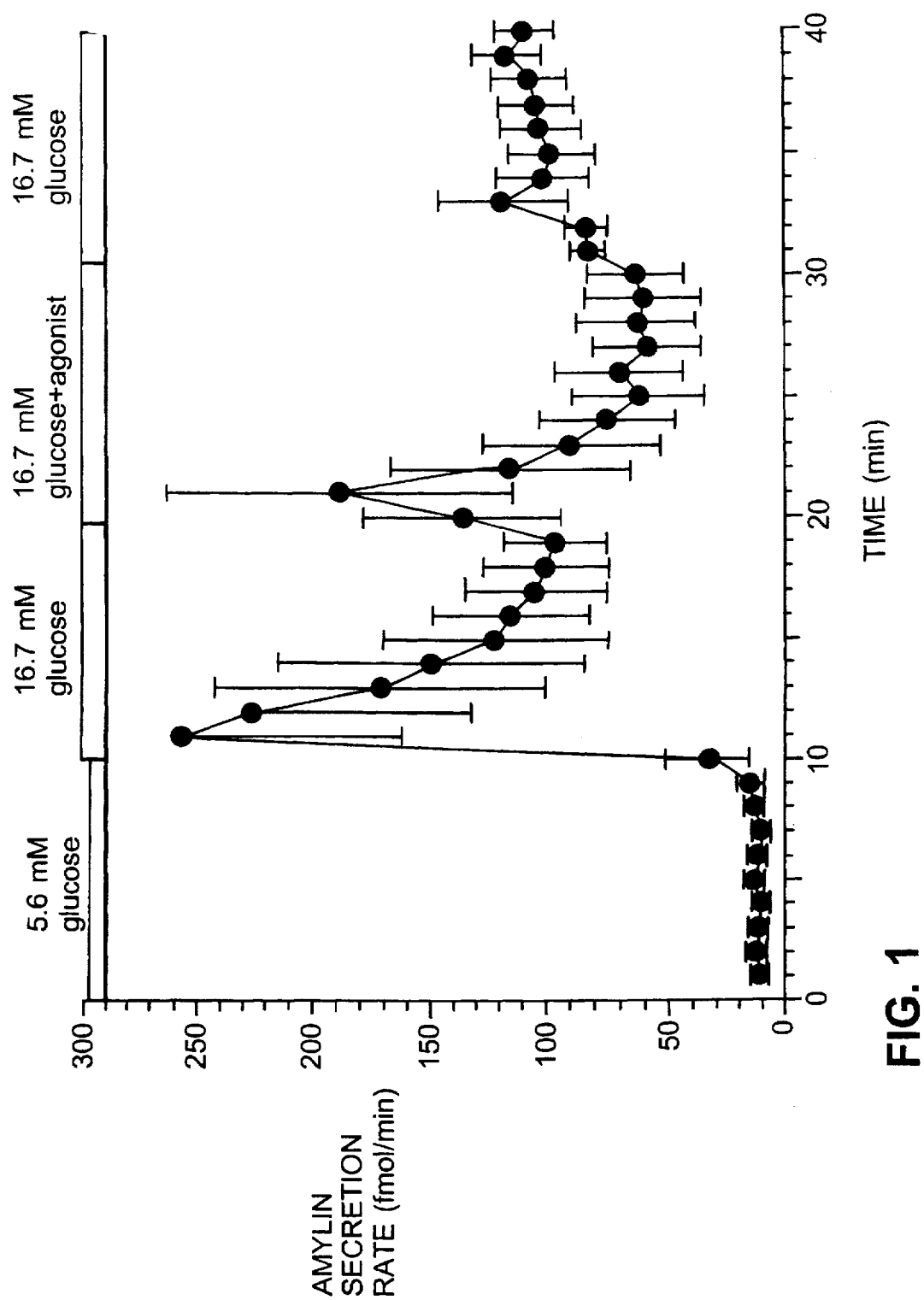
FIG. 1 is a graph showing the effect of somatostatin-14 on glucose-induced amylin secretion.

A SSTR-5 agonist which can be used to practice the therapeutic method of the present invention is a somatostatin receptor ligand which is more selective for SSTR-5 than for SSTR-2. Selectivity of a SSTR-5 agonist for a particular receptor is determined by receptor binding assays, in which its respective binding inhibition constants ($K_i$'s) for SSTR-5 and SSTR-2 are determined. The SSTR-5 agonists which are capable of inhibiting amylin secretion are those compounds having either (i) a $K_i$ for the human SSTR-5, as determined by utilizing CHO-K1 cells transfected with the human SSTR-5, which is lower than that for the human SSTR-2, as determined by utilizing CHO-K1 cells transfected with the human SSTR-2, or (ii) a $K_i$ for the rat SSTR-5, as determined by utilizing rat olfactory bulb cells, which is lower than that for the rat SSTR-2, as determined by utilizing AR42J rat pancreatic acinar tumor cells. The just-mentioned four binding assays are described in detail in the working examples below. A preferred SSTR-5 agonist is at least 3 times as selective for SSTR-5 as for SSTR-2; in other words, its ratio of $K_i$ for SSTR-2 to $K_i$ for SSTR-5 is 3 or higher (e.g., 10,000) in either the human system or the rat system. An even more preferred SSTR-5 has a selectivity for SSTR-5 10 times or higher (e.g., 10,000) that of that for SSTR-2.

Preferably, the above-mentioned SSTR-5 agonists are linear peptides. Examples of such linear peptides include, but are not limited to, those covered by the following generic formula:

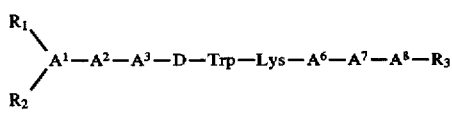

wherein $A^1$ is a D- or L- isomer of Ala, Leu, Ile, Val, Nle, Thr, Ser, β-Nal, β-Pal, Trp, Phe, 2,4-dichloro-Phe, pentafluoro-Phe, p-X-Phe, or o-X-Phe, wherein X is $CH_3$, Cl, Br, F, OH, $OCH_3$, or $NO_2$;

$A^2$ is Ala, Leu, Ile, Val, Nle, Phe, β-Nal, pyridyl-Ala, Trp, 2,4-dichloro-Phe, pentafluoro-Phe, o-X-Phe, or p-X-Phe, wherein X is $CH_3$, Cl, Br, F, OH, $OCH_3$, or $NO_2$;

$A^3$ is pyridyl-Ala, Trp, Phe, β-Nal, 2,4-dichloro-Phe, pentafluoro-Phe, o-X-Phe, or p-X-Phe, wherein X is $CH_3$, Cl, Br, F, OH, $OCH_3$, or $NO_2$;

$A^6$ is Val, Ala, Leu, Ile, Nle, Thr, Abu, or Ser;

$A^7$ is Ala, Leu, Ile, Val, Nle, Phe, β-Nal, pyridyl-Ala, Trp, 2,4-dichloro-Phe, pentafluoro-Phe, o-X-Phe, or p-X-Phe, wherein X is $CH_3$, Cl, Br, F, OH, $OCH_3$, or $NO_2$;

$A^8$ is a D- or L- isomer or Ala, Leu, Ile, Val, Nle, Thr, Ser, Phe, β-Nal, pyridyl-Ala, Trp, 2,4-dichloro-Phe, pentafluoro-Phe, p-X-Phe, or o-X-Phe, wherein X is $CH_3$, Cl, Br, F, OH, $OCH_3$, or $NO_2$;

each $R_1$ and $R_2$, independently, is H, lower acyl or lower alkyl; and $R_3$ is OH or $NH_2$; provided that at least one of $A^1$ and $A^8$ and one of $A^2$ and $A^7$ must be an aromatic amino acid; and further provided that $A^1$, $A^2$, $A^7$, and $A^8$ cannot all be aromatic amino acids.

Examples of linear SSTR-5 agonists to be used in the therapeutic method of this invention include:

H-D-Phe-Phe-Phe-D-Trp-Lys-Thr-Phe-Thr-$NH_2$ (BIM-23052);

H-D-Phe-Phe-Phe-D-Trp-Lys-Thr-Phe-Thr-OH (Analog I);

H-D-Phe-p-chloro-Phe-Tyr-D-Trp-Lys-Thr-Phe-Thr-$NH_2$;

H-D-Phe-p-$NO_2$-Phe-Tyr-D-Trp-Lys-Val-Phe-Thr-$NH_2$;

H-D-Nal-p-chloro-Phe-Tyr-D-Trp-Lys-Val-Phe-Thr-$NH_2$;

H-D-Phe-Phe-Tyr-D-Trp-Lys-Val-Phe-Thr-$NH_2$;

H-D-Phe-p-chloro-Phe-Tyr-D-Trp-Lys-Val-Phe-Thr-$NH_2$;

H-D-Phe-Ala-Tyr-D-Trp-Lys-Val-Ala-D-p-Nal-$NH_2$; and

H-D-Phe-Phe-Tyr-D-Trp-Lys-Val-Phe-D-Phe-$NH_2$ .

If desired, one or more chemical moieties, e.g., a sugar derivative, mono or poly-hydroxy $C_{2-12}$ alkyl, mono or poly-hydroxy $C_{2-12}$ acyl groups, or a piperazine derivative, can be attached to a SSTR-5 agonist, e.g., to the N-terminus amino acid. See PCT Application WO 88/02756, European Application 0 329 295, and PCT Application WO 94/08875. An example of a SSTR-5 agonist which contains an N-terminal chemical substitution is:

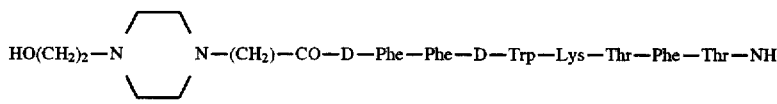

(Analog II)

Note that, unless indicated otherwise, for all amino acid sequence formulas described herein, each amino acid residue, e.g., $A^1$ or Lys, represents the structure of NH—C(R)H—CO—, in which R is the side chain. Lines between amino acid residues represent peptide bonds which join two amino acids. Also, where the amino acid residue is optically active, it is the L-form configuration that is intended unless D-form is expressly designated. The uncommon abbreviations β-Nal, β-Pal, Nle, and Abu stand for, respectively, 3-(β-naphthyl)alanine, 3-(β-pyridyl)alanine, norleucine, and α-aminobutyric acid.

Without further elaboration, it is believed that one skilled in the art can, based on the description herein, utilize the present invention to its fullest extent. Indeed, unless defined otherwise, all technical and scientific terms used herein have the same meaning as commonly understood by one of ordinary skill in the art to which this invention belongs. Methods and materials similar or equivalent to those described herein can be used in the practice or testing of the present invention. All publications, patent applications, patents, and other references mentioned herein are incorporated by reference. In addition, the materials, methods, and examples are illustrative only and not intended to be limiting.

Synthesis of somatostatin receptor ligands

Synthesis of short amino acid sequences is well established in the peptide art. For example, synthesis of BIM-23052, structure of which is described above, can be achieved by following the protocol set forth in Example I of European Patent Application 0 395 417 A1. The synthesis of somatostatin analogs with a substituted N-terminus can be achieved, for example, by following the protocol set forth in WO 88/02756, European Patent Application No. 0 329 295, and PCT Application No. WO 94/08875.

SSTR-5 agonists such as Analogs I and II can be synthesized in an similar manner.

Synthesis of radiolabeled somatostatin receptor ligands

The synthesis of radiolabeled somatostatin receptor ligands is well documented and are within the ability of a person of ordinary skill in the art. See, e.g., Czernick, et al., J. Biol. Chem. 258:5525 (1983). For example, the SSTR-2 radioligand, cyclo (N-Me-Ala-Tyr[$I^{125}$]-D-Trp-Lys-Val-Phe) or [$^{125}$I-Tyr]MK-678, was synthesized in the manner set forth below: The uniodinated cyclic hexapeptide was first synthesized according to the procedure set forth in U.S. Pat. No. 4,310,518. The hexapeptide was then iodinated utilizing the chloramine-T method. More specifically, 50 nM of sodium phosphate buffer (pH 7.4, 50 µl), a solution of MK-678 (1 mM in phosphate buffer, 10 µl), and $Na^{125}I$ (1 mCi in approximately 10 µl of $H_2O$) were added to a polypropylene tube. The reaction was started by addition of a freshly prepared chloramine-T solution (1 mg/ml in $H_2O$; 10 µl). The mixture was agitated for 30 sec and then a solution of cysteine in phosphate buffer (2 mg/ml; 100 µl) was added to stop the reaction. The material was purified by HPLC. Fractions containing the desired product were identified by UV detection at 214 nM on a 20–50% gradient for 30 min, pooled, diluted with 10% ethanol, and stored at –20° C.

Another radiolabeled somatostatin receptor ligand [$^{125}$I-Tyr$^{11}$]somatostatin-14 can be prepared following a similar procedure. [$^{125}$I-Tyr$^{11}$]somatostatin-14 is also commercially available.

Somatostatin receptor binding assays (1) Rat SSTR-2 Binding Assay

Crude membranes were prepared by homogenizing AR42J cells (ATCC, Rockville, Md.; ATCC No. CRL1992) in 20 ml of ice-cold 50 mM Tris-HCl (Buffer A) with a POLYTRON homogenizer (Brinkmann Instruments, Westbury, N.Y.) at setting 6, for 15 sec. Additional Buffer A was added to obtain a final volume of 40 ml, and the homogenate was centrifuged in a Sorval SS-34 rotor (DuPont, Newtown, Conn.) at 39,000 g for 10 min at 0°–4° C. The resulting supernatant was decanted and discarded. The pellet was rehomogenized in ice-cold Buffer A, diluted, and centrifuged as before. The final pellet was resuspended in the 10 mM Tris HCl and held on ice for the receptor binding assay.

Aliquots of the membrane preparation were incubated for 90 min at 25° C. with 0.05 nM [$^{125}$I-Tyr]MK-678 (2000 Ci/mmol) in 50 mM HEPES (pH 7.4) containing a test peptide of various concentrations (e.g., $10^{-11}$ to $10^{-6}$ M), 10 mg/ml bovine serum albumin (fraction V) (Sigma Chemical Co., St. Louis, Mo.), $MgCl_2$ (5 mM), Trasylol (200 KIU/ml), bacitracin (0.02 mg/ml), and phenylmethyl-sulphonyl fluoride (0.02 mg/ml). The final assay volume was 0.3 ml. The incubations were terminated by rapid filtration through GF/C filters (pre-soaked in 0.3% polyethylenimine for 30 min) using a filtration manifold (Brandel, Gaithersburg, Md.). Each tube and filter was then washed three times with 5 ml aliquots of ice-cold Buffer A. Specific binding was defined as the total [$^{125}$I-Tyr]MK-678 bound somatostatin-14 bound minus that bound in the presence of 200 nM somatostatin-14.

The following somatostatin analogs were assayed: somatostatin-14, Analog I (structure shown above), Analog II (structure shown above), BIM-23052 (structure shown above), BIM-23014 (H-D-β-Nal-Cys-Tyr-D-Trp-Lys-Val-Cys-Ser-$NH_2$; LANREOTIDE or SOMATULINE), and SMS 201–995 (H-D-Phe-Cys-Phe-D-Trp-Lys-Thr-Cys-Threoninol; SANDOSTATIN or OCTREOTIDE). The $K_i$ values for these test somatostatin analogs were calculated by using the following formula: $K_i=IC_{50}/[1+(LC/LEC)]$ where $IC_{50}$ is the concentration of test compound required to inhibit 50 percent of the specific binding of the radioligand [$I^{125}$-Tyr]MK-678, LC is the concentration of the radioligand (0.05 nM), and LEC is the equilibrium dissociation constant of the radioligand (0.155 nM). The $K_i$ values calculated for the tested peptides are shown in the column under the heading "SSTR-2" in Table I.

(2) Rat SSTR-5 Binding Assay

Crude membranes were prepared by homogenization of rat olfactory bulb cells (Zivic-Miller Laboratory, Inc., Zellenople, Pa.) in 20 ml of ice-cold 50 mM Tris-HCl with a POLYTRON homogenizer (setting 6, 15 sec). Buffer was added to obtain a final volume of 40 ml, and the homogenate was centrifuged in a Sorval SS-34 rotor at 39,000 g for 10 min at 0°–4° C. The resulting supernatant was decanted and discarded. The pellet was rehomogenized in ice-cold buffer, diluted, and centrifuged as before. The final pellet was resuspended in the 10 mM Tris HCl and held on ice for the receptor binding assay.

Aliquots of the membrane preparation were incubated for 30 min at 30° C. with 0.05 nM [$^{125}$I-Tyr$^{11}$]somatostatin-14 (2000 Ci/mmol; Amersham Corp., Arlington Heights, Ill.) in 50 mM HEPES (pH 7.4) containing a test peptide of various concentrations (e.g., $10^{-11}$ to $10^{-6}$ M), 10 mg/ml bovine serum albumin (fraction V) (Sigma Chemical Co., St. Louis, Mo.), MgCl$_2$ (5 mM), Trasylol (200 KIU ml), bacitracin (0.02 mg/ml), and phenylmethylsulphonyl fluoride (0.02 mg/ml). The final assay volume was 0.3 ml. The incubations were terminated by rapid filtration through GF/C filters (pre-soaked in 0.3% polyethylenimine for 30 min) using a Brandel filtration manifold. Each tube and filter were then washed three times with 5 ml aliquots of ice-cold buffer. Specific binding was defined as the total [$^{125}$I-Tyr$^{11}$] somatostatin-14 bound minus that bound in the presence of 1000 nM BIM-23052. The $K_i$ values for the tested somatostatin-14 and its analogs were calculated by using the following formula: $K_i=IC_{50}/[1+(LC/LEC)]$ where $IC_{50}$ is the concentration of test compound required to inhibit 50 percent of the specific binding of the radioligand [$^{125}$I-Tyr$^{11}$] somatostatin-14, LC is the concentration of the radioligand (0.05 nM), and LEC is the equilibrium dissociation constant of the radioligand (0.16 nM). The $K_i$ values for the tested somatostatin analogs are shown in the column under the heading "SSTR-5" in Table I.

Table I also shows the respective ratios of the $K_i$'s for the rat SSTR-2 and the $K_i$'s for the rat SSTR-5. Thus, those somatostatin analogs with such ratios greater than one (e.g., BIM-23052, Analog I, and Analog II) are more selective for the rat SSTR-5 than for SSTR-2.

TABLE I

| COMPOUND | SSTR-2 | SSTR-5 | SSTR-2/SSTR-5 |
|---|---|---|---|
| BIM-23052 | 8.04 | 3.16 | 2.54 |
| Analog I | 37.2 | 3.57 | 10.4 |
| Analog II | 305 | 5.38 | 56.7 |
| Somatostatin-14 | 0.17 | 0.47 | 0.34 |
| SMS 201-995 | 0.38 | 9.14 | 0.04 |
| BIM-23014 | 0.34 | 64.8 | 0.005 |

(3) Human SSTR-2 Binding Assay

The human SSTR-2 cDNA clone has been described (Yamada, et al., Proc. Natl. Acad. Sci. USA., 89:251–255 (1992)) and is available from ATCC (ATCC No. 79046). A 1.7 kilobase BamHI-HindIII fragment containing the entire coding region of the human SSTR-2 receptor has been isolated by restriction endonuclease digestion and is available from New England Biolabs (Beverly, Mass.). This CDNA fragment was inserted into the mammalian expression vector, pCMV (Russell, et al., J. Biol. Chem., 264:8222–8229 (1989)) using standard molecular biology techniques to produce the expression plasmid, pCMV-human SSTR-2. Other mammalian expression vectors include pcDNA1/Amp (Invitrogen,' Sandlesy, Calif.). See, e.g., Maniatis, et al., Molecular Cloning, A Laboratory Manual, Cold Spring Harbor Laboratory, 1982. The expression plasmid was introduced into the suitable bacterial host, E. Coli HB101 (Stratagene, La Jolla, Calif.) and plasmid DNA, for transfection, was prepared on a Cesium Chloride gradient.

CHO-K1 (ovary, Chinese hamster) cells were obtained from the American Type Culture Collection, Rockville, Md. (ATCC No. CCL 61). The cells were grown and maintained in Ham's F12 media (Gibco BRL, Grand Island, N.Y.) supplemented with 10% fetal bovine serum under standard tissue culture conditions.

For transfection, the cells were seeded at a density 1×10$^6$/60 cm$^2$ plate (Baxter Scientific Products, McGaw Park, Ill.). DNA mediated transfection was carried out using the calcium phosphate co-precipitation method (Ausubel, et al., Current Protocols in Molecular Biology, John Wiley & Sons, 1987). The plasmid pRSV-neo (ATCC; ATCC No. 37198) was included as a selectable marker at 1/10 the concentration of the expression plasmid. CHO-K1 clonal cell lines that have stably inherited the transfected DNA were selected for growth in Ham's F12 media containing 10% fetal bovine serum and 0.5 mg/ml of G418 (Sigma Chemical Co., St. Louis, Mo.). The cells were ring-cloned and expanded in the same media for analysis.

Expression of the human SSTR-2 receptor was be detected by Northern blot analysis of total RNA prepared from the cells (Sambrook, et al., Molecular Cloning—A Laboratory Manual, Ed. 2., Cold Spring Harbor Laboratory, Cold Spring Harbor, N.Y., 1989) and by receptor binding using [$^{125}$I-Tyr$^{11}$]somatostatin-14 as a ligand. Transfected cell lines expressing the human SSTR-2 receptor were clonally expanded in culture and used in the rat SSTR-2 binding protocol described above. The $K_i$ for the test somatostatin analogs are listed in Table II (where LC is 0.05 nM and LEC is 0.15 nM).

(4) Human SSTR-5 Binding Assay

The human SSTR-5 cDNA clone has been described in the literature. See Panetta, et al., Mol Pharmacol., 45:417–427 (1994); O'Carroll, et al., Mol Pharmacol., 46:291–298 (1994); Yamada, et al., Biochem. Biophys. Res. Commun., 195:844 (1993) wherein FIG. 1 depicts the DNA sequence of the human SSTR-5. Using a sense 5'-oligonucleotide primer, immediately preceeding the start codon (residue 30–50), and an antisense 3'-oligonucleotide primer, immediately preceeding the stop codon (residues 1180–1200), a 1170 base pair fragment comprising the full-length coding sequence of the receptor was obtained by standard Reverse-transcription PCR. See Yamada, et al., Biochem. Biophys. Res. Commun., 195:844 (1993) wherein FIG. 1 depicts the DNA sequence of the human SSTR-5; Innis, et al., PCR Protocols, A Guide to Methods and Applications, Academic Press, 1990. The identity of the cDNA fragment was verified by DNA sequencing using the dideoxy-chain termination method [Sanger, et al., Proc Natl Acad Sci USA., 74:5463 (1977)] with the Sequenase kit (United States Biochemicals, Arlington Heights, Ill).

The human SSTR-5 cDNA fragment was inserted into a mammalian expression vector, pCMV to generate the expression plasmid pCMV-human SSTR-5 by blunt-end ligation. See e.g., Maniatis, et al., Molecular Cloning-A Laboratory Manual, Cold Spring Harbor Laboratory, Cold Spring Harbor, N.Y., 1982.

The expression plasmid was transfected into CHO-K1 cells as described in Example 3 and clonal cell lines were selected and characterized for the expression of the human SSTR-5 receptor by Northern blot analysis and ligand-binding using [$^{125}$I-Tyr$^{11}$]somatostatin-14. A cell line, CHO-K1M, was shown to express the human SSTR-5. Membranes from the stably transfected cell line were used in the rat SSTR-5 binding protocol described above. The $K_i$ for the test somatostatin analogs are listed in Table II (where LC is 0.05 nM and LEC is 0.18 nM).

TABLE II

| COMPOUND | SSTR-2 | SSTR-5 | SSTR-2/SSTR-5 |
| --- | --- | --- | --- |
| BIM-23052 | 14.1 | 1.22 | 11.5 |
| Analog I | 14.2 | 12.4 | 1.14 |
| Analog II | 4.15 | 1.29 | 3.22 |
| Somatostatin-14 | 0.18 | 0.86 | 0.20 |
| BIM-23014 | 1.09 | 5.2 | 0.21 |
| SMS 201-995 | 0.5 | 7.0 | 0.07 |

Amylin release inhibition assay using rat pancreas cells

Sprague-Dawley rats (male, 200–300 g) (Harlan-Olac, Bicester, Oxon, UK) were anaesthetized with sodium pentobarbitone (60 mg/kg). The pancreases of the rats were isolated as previously described in Dunmore, et al., J. Endocrinol. 92:15–20 (1982). The pancreases were perfused, as described in Dunmore, et al., J. Endocrinol., 1993, 137, 375–381, with modified Krebs-Ringer bicarbonate buffer containing 3% dextran T40 (Pharmacia, Milton Keynes, Bucks, UK) and 1% high purity bovine serum albumin (Sigma, Poole, Dorset, UK). After an initial 15-min period to allow for stabilization, the isolated pancreases were perfused at sequential 10 min. intervals, at a rate of 4.5–5.0 ml/min, with the following buffer compositions: 1) Buffer 1: Krebs-Ringer bicarbonate buffer containing 5.6 mM glucose (to examine baseline amylin secretion); 2) Buffer 2: Krebs-Ringer bicarbonate buffer containing 16.7 mM glucose (to examine high glucose stimulated secretion); 3) Buffer 3: Krebs-Ringer bicarbonate buffer containing 16.7 mM glucose in the presence of 10 nM of test compound (to examine the activity of test compounds on high glucose stimulated amylin secretion); and 4) Buffer 2: Krebs-Ringer bicarbonate buffer containing 16.7 mM glucose (to re-examine high glucose stimulated amylin secretion in order to assess the reversibility of the activity of the test compounds).

Fractions of the perfusate were collected on ice every minute in the presence of 400 KIU/ml aprotinin (Bayer, Hayward's Heath, W. Sussex, UK). Fractions were stored at −20° C. until assay. Perfusates collected were divided into 3×1.5 ml aliquots and assayed for amylin by radioimmunoassay as described in Dunmore, et al., J. Endocrinol., 1993, 137:375. Amylin was assayed using reagents supplied by Peninsula Laboratories Ltd. (St. Helens, Merseyside, UK). These reagents include $^{125}$I-labelled amylin, rabbit anti-rat amylin antibody, and rat amylin. Bound amylin was precipitated using goat anti-rabbit second antibody-coupled cellulose (Sac-Cal, IDS, Boldon, Tyneawear, UK).

Figure 2:
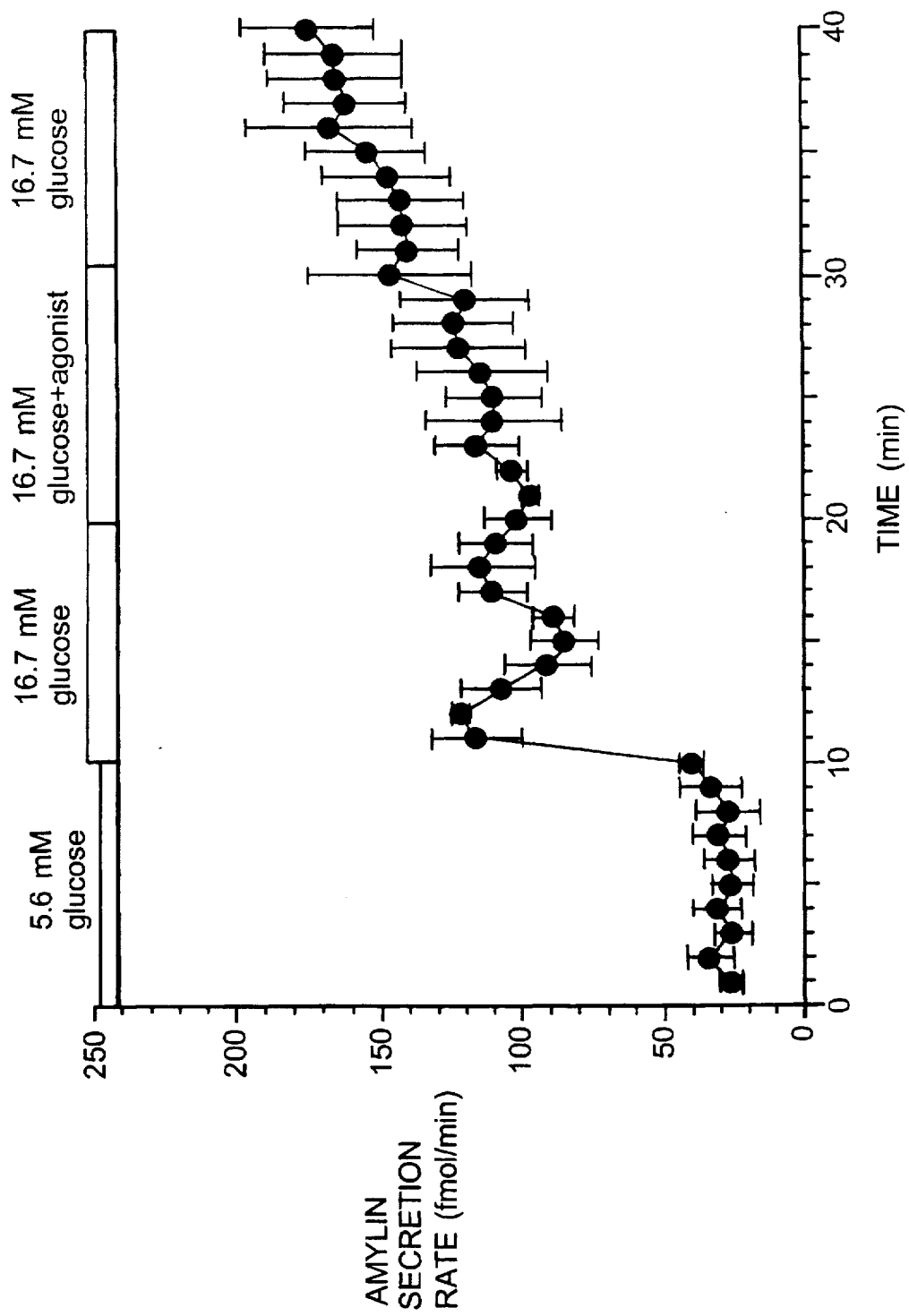
FIG. 2 is a graph showing the effect of a somatostatin analog on glucose-induced amylin secretion.
Figure 3:
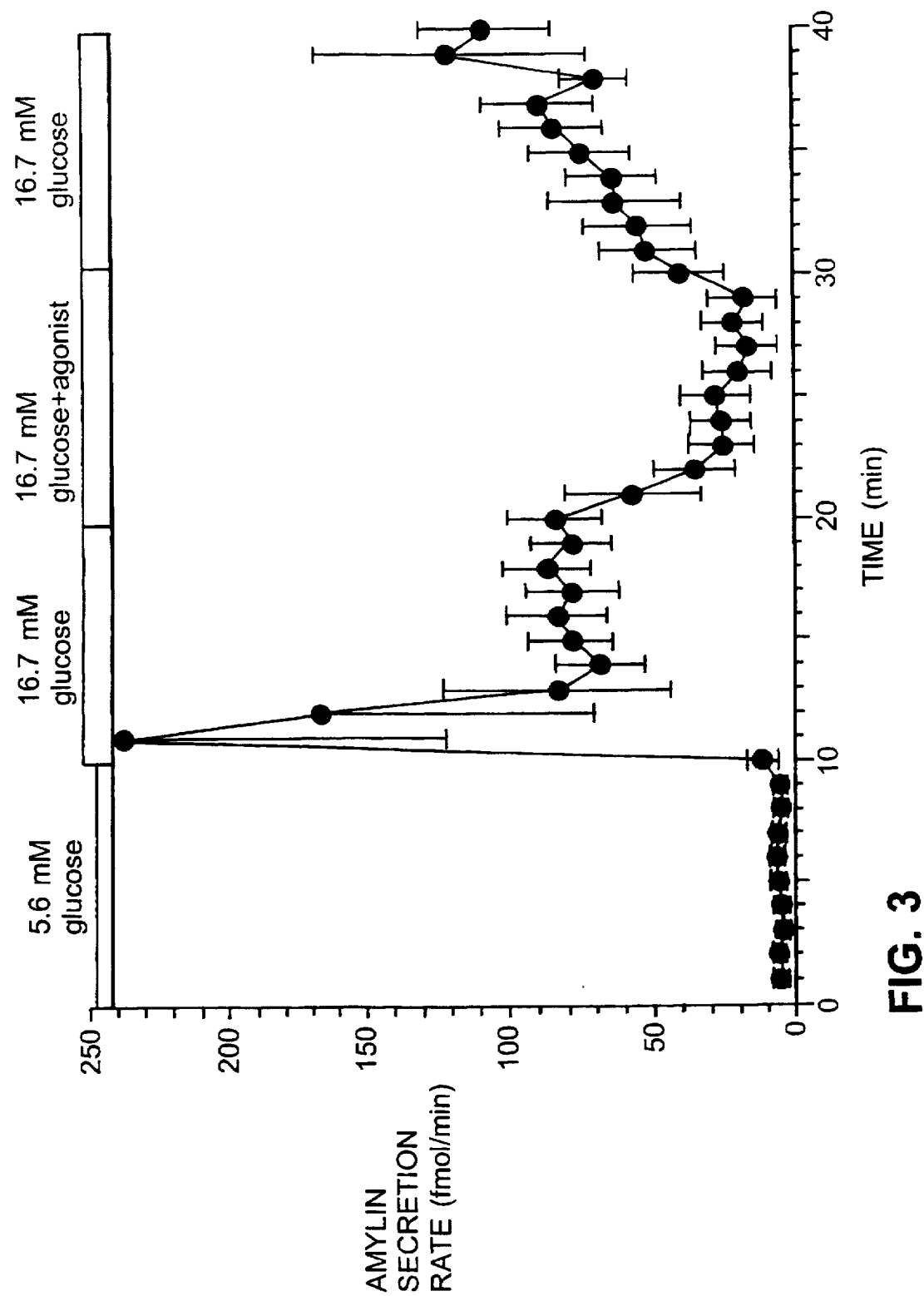
FIG. 3 is a graph showing the effect of another somatostatin analog on glucose-induced amylin secretion.

Somatostatin-14, BIM-23014, and BIM-23052 were used as test compounds in the above assay. The results of the assay are presented in FIGS. 1–3. In all cases, perfusion of the isolated rat pancreas with 16.7 mM glucose produced a significant increase in amylin secretion. Somatostatin-14, which possesses a high affinity for SSTR-5, inhibited glucose-induced amylin secretion at 10 nM (FIG. 1). Somatostatin analog BIM-23014, which possesses a low affinity for SSTR-5, had no effect at the same concentration (FIG. 2). In sharp contrast, BIM-23052, which possesses a high affinity for SSTR-5 and a low affinity for SSTR-2, produced a 78% decrease in glucose stimulated amylin secretion at the same concentration (FIG. 3). The above assay can also be performed using rat pancreases isolated from female Zucker fatty rats (Harlan-Olac, Bicester, Oxon, UK).

Amylin release inhibition assays using RINm5f cells

The establishment and culture of the rat β-cell line RINm5f cells has been previously described. See Gazdar, et al., Proc. Natl. Acad. Sci. USA., 77:3519 (1980); Praz, et al., Biochem. J., 210:345 (1983). For an in vitro amylin release inhibition assay, RINm5f cells, passage 19–21 are used. The cells, available from the National Institute of Health, Bethesda, Md.), are maintained under standard tissue culture conditions in RPMI-1640 medium supplemented with 2% fetal bovine serum and 2 mM of glutamine.

For the assessment of amylin release, cells are seeded at $3 \times 10^5$ cells/well in 24-well plates (Baxter Scientific Products, McGaw Park, Ill.). After 36–48 hours in culture at 37° C., the media is removed and replaced with 500 µl of Kreb-Ringer buffer containing 2 mM glucose, 1 mg/ml BSA (Sigma A-4378, Sigma Chemical Co., St. Louis, Mo.) at a pH of 7.4 for 30 min. Moore, et al., Biochem. Biophys. Res. Commun., 179:1 (1993). At the end of that period, the buffer is replaced with 1 ml of fresh buffer containing either 15 mM D-glyceraldehyde or 50 mM DL-glyceraldehyde (Sigma Chemical Co., St. Louis, Mo.) in the presence or absence of test compounds. At the end of a two-hour incubation at 37° C., the buffer is recovered, centrifuged at 700 rpm for 5 min, and assayed for amylin content as previously described. Dunmore, et al., J Endocrinol., 137:375 (1993).

Other Embodiments

The foregoing description has been limited to specific embodiments of this invention. It will be apparent, however, that variations and modifications may be made to the invention, with the attainment of some or all of the advantages of the invention. Such embodiments are also within the scope of the following claims.

What is claimed is:

1. A method of determining the ability of a compound to both bind to somatostatin type-5 receptor and inhibit amylin release from amylin-secreting pancreas cells, said method comprising:

obtaining CHO-K1 cells transfected with DNA encoding the human somatostatin type-5 receptor or a membrane preparation obtained therefrom;

incubating said CHO-K1 cells or a membrane preparation obtained therefrom, said compound, and a somatostatin type-5 receptor ligand, at least one of said ligand and said compound being detectably labeled;

determining the ability of said compound to compete against said ligand for binding to somatostatin type-5 receptor;

if and only if said compound binds to somatostatin type-5 receptor; obtaining amylin-secreting pancreatic cells;

incubating said compound, said pancreatic cells, and an amylin release stimulator under conditions in which said amylin release stimulator would induce release of amylin from said pancreatic cells; and determining the ability of said compound to inhibit amylin release.

2. A method of claim 1, wherein said ligand is detectably labeled.

3. A method of claim 1, wherein said amylin-secreting pancreatic cells are pancreatic islet cells.

4. A method of claim 3, wherein said pancreatic islet cells are β cells.

5. A method of claim 1, wherein said pancreatic cells are cells in an isolated rodent pancreas.

* * * * *